United States Patent [19]

Janchitraponvej et al.

[11] Patent Number: 5,985,256
[45] Date of Patent: Nov. 16, 1999

[54] HAIR DRESSING COMPOSITION

[75] Inventors: Ben Janchitraponvej, Niles; Arun Nandagiri, Libertyville, both of Ill.

[73] Assignee: Helene Curtis, Inc., Chicago, Ill.

[21] Appl. No.: 08/897,961

[22] Filed: Jul. 21, 1997

[51] Int. Cl.⁶ ........................................................ A61K 7/06
[52] U.S. Cl. .................... 424/70.28; 424/401; 424/70.2; 424/47
[58] Field of Search .................................. 424/401, 70.2, 424/70.28, 47

[56] References Cited

U.S. PATENT DOCUMENTS 5,164,177  11/1992  Bhatt et al. ............................... 424/47
5,674,478  10/1997  Dodd et al. .............................. 424/70.1

OTHER PUBLICATIONS

Allied Colloids Product Sheet for Salcare SC 96 (5 pages).
Label for Bouncy Creme Styling Aid.

*Primary Examiner*—Jyothsna Venkat
*Attorney, Agent, or Firm*—Matthew Boxer

[57] ABSTRACT

The present invention is directed to an aqueous hair dressing or hair styling composition which comprises from about 1.5 to about 5.0 weight % polyquaternium 37/propylene glycol dicaprylate dicaprate and ppg-1 trideceth-6, also known as polyquat 37, and also known as Salcare 96. The compositions of the invention have good hair styling and manageability properties without tackiness.

2 Claims, No Drawings

HAIR DRESSING COMPOSITION

FIELD OF THE INVENTION

This invention relates to an aqueous hair dressing composition that provides good hair styling and manageability properties without tackiness. Since hair dressing compositions are usually applied by hand, tackiness or stickiness is an unpleasant and undesirable property for hair dressing compositions to have.

BACKGROUND OF THE INVENTION

Hair dressing compositions are known in the art. They are usually solutions containing a hair styling or holding polymer in a suitable vehicle such as alcohol and/or water along with auxiliary conditioning agents such as silicones, esters, and the like, to provide the required film forming properties. In such compositions, the styling resins provide the desired hair styling properties whereas the auxiliary conditioning agents are there to modify the film properties to make them pliable and hair manageable. Hair dressing compositions are applied by placing a small amount in the palm of the hands, spreading evenly by rubbing the palms together, and applying the composition to the hair. Since the product is applied with the users' hands, a common complaint of such compositions are that they are very tacky and sticky. It is this stickiness that is responsible for the good styling that compositions provide. Polymers having less stickiness are available, but they do not have the desired film forming properties. Also, the tackiness of the high film formers can be modified by the use of auxiliary ingredients such as silicones and esters, but the addition of these compounds detracts from the styling properties. To overcome some of these drawbacks, formulators have also attempted to put these resins into emulsions where the water base containing the styling resins is emulsified in the oil phase containing silicones or oils. While these compositions have improved non-sticky properties they still effect the styling properties of the resin. Hair styling compositions described above are available in the commercial market under trade names such as BRYLCREAM, ALBERTO VO5. They are also described in various text books such as Harry's Cosmetology.

SUMMARY OF THE INVENTION

The present invention is directed to an aqueous hair dressing or hair styling composition which comprises from about 1.5 to about 5.0 weight % polyquat 37 also known as polyquaternium 37/propylene glycol dicaprylate dicaprate and ppg-1 tri deceth-6, also sold as Salcare SC96. Salcare SC96 is supplied as 48–52% active in a carrier ester. The weight per cents Salcare SC96 discussed herein are as supplied in the carrier solution.

Preferred ranges of Sal care SC 96 are from about 1.5 to about 4.0 weight %, and 2.0 to about 4.0 weight % and 3.0 to about 5.0 weight %.

The invention also relates to a method for styling or dressing the hair which comprises application to the hair of the compositions of the invention.

An object of the present invention is to provide hair dressing or hair styling compositions with good hair styling properties but without stickiness to the hands. A second object of the invention is to provide a range of compositions where the styling properties can be varied depending upon the needs of the individual hair types while maintaining the nonsticky profile. A third object of the invention is to provide hair dressing or styling compositions for individuals with high styling needs which can be obtained by using higher polymer levels (Salcare SC96) and also auxiliary detackifying agents so as to lower the stickiness of the resulting compositions. A fourth object of the invention is a composition which can be used on hair and the hair does not develop static. A fifth object of the invention is to provide a composition which can be used to dress thin hair so that the resulting thin hair has no flyaway tendencies. A sixth object of the invention is to provide a composition, which when used on hair that is exposed to high humidity or is either prewet or wet, does not cause the hair to feel sticky.

DETAILED DESCRIPTION OF THE INVENTION

The present invention is directed to a hair dressing or hair styling composition which comprises from about 1.5 to about 5.0 weight % polyquaternium 37/propylene glycol dicaprylate dicaprate and ppg-1 trideceth-6, also sold as Salcare SC96. Preferred ranges of Salcare SC96, are about 1.5 to about 4.0 weight % and 2.0 to about 4.0 weight % and 3.0 to about 4.0 weight %.

The compositions of the invention may also contain a glycol such as propylene glycol. Propylene glycol may be added to compositions of the invention in a range of about 2.0 to about 10.0% propylene glycol. Short chain isopropyl esters may be added to compositions of the invention in a range of about 1.0 to about 10.0%. Exemplary of such short chain isopropyl esters are isopropyl palmitate or isopropyl myristate or mixtures thereof.

The invention also relates to a method for styling or dressing the hair which comprises application to the hair of the compositions of the invention.

Salcare SC96 which is used in the compositions of the invention is a high cationic charged polymer dispersed in a carrier ester. It has the following technical names: ethanaminium N,N,N-trimethyl-2-[(methyl-1-oxo-2-propenyl)oxy]-chloride, homopolymer and N,N,N-trimethyl-2-[(methyl-1-oxo-2-propenyl)oxy] ethanaminium chloride, homopolymer.

The compositions of the invention may also optionally contain a preservatives, proteins and vitamins, and fragrances Salcare SC 96 has excellent hair styling properties while at the same time, it has very low stickiness. When compositions are desired having a higher level of hold, Salcare SC 96, could be used at a higher level (5.0% or higher), with auxiliary detackifing agents such as short chain fatty acid esters.

Specific examples of compositions of the invention (A, B, C, D and F) were made as follows:

COMPOSITIONS OF THE INVENTION

| Ingredients | A | B | C | D | E | F |
|---|---|---|---|---|---|---|
| Water, soft | 98.25 | 97.25 | 96.75 | 95.75 | 94.75 | 89.75 |
| Salcare SC 96 | 1.50 | 2.50 | 3.0 | 4.0 | 5.0 | 5.0 |
| Isopropyl Palmitate | — | — | — | — | — | 2.50 |
| Isopropyl Myristate | — | — | — | — | — | 1.50 |
| Preservative | .25 | .25 | .25 | .25 | .25 | .25 |

Procedure for Preparing Compositions of the Invention:
1.) Water was added to the beaker.
2.) A mixer in the beaker was turned on and adjusted to a rate or speed of mixing to avoid splashing.
3.) The following items were added in the order in which they are written below:
   i). Salcare SC96
   ii). Isopropyl Palmitate (where applicable)
   iii). Isopropyl Myristate (where applicable)
   iv). Preservative.

In extensive tests with this polymer we have found that it could be used to provide hair styling and manageability benefits when it is used at a level higher than 2.5%. More importantly we hare finding that this polymer has the desired styling and manageability benefits without tackiness. The styling properties start to show at a level as low as 1.5% and increase with increased levels of the resin up until 5.0%. At the levels tested, we see no tack to these formulas and increased level of styling properties. As a styling composition we see that at 5.0% it gives more than the desired level of styling benefit. For those individual hair types such as damaged and porous hair where there is a good absorption of the polymer, levels higher than 5.0% may be required and at this level auxiliary detack agents may be required to maintain the non tack properties seen with lower polymer formulations. This can be done by incorporating conventional additives such as silicones, esters, oils known in the art. The major difference, however, is that the incorporation of these materials does not detract or adversely effect the styling porperties of this polymer.

To demonstrate the non-tackiness properties of this polymer experiments were performed using the Diastron MTT 160 Tensile Tester equipped with the supplied tack testing plates. This apparatus tests the tackiness of a formulation by measuring the forces between two circular stainless steel plates which are repeatedly pressed together. The upper plate contains a ball and socket joint which allows the parallel orientation of the two plates. A spring contained in the lower plate gives a compliance to the system as the plates are driven together.

Experiments were performed using the instrumental settings recommended in the Diastron manual. These parameters are given below.

| Contact time: | 2 seconds | Rate: | 150 mm/min |
|---|---|---|---|
| Cyclic separation: | 10 mm | Maximum Force: | 2000 gmf |
| Contact time: | 2 seconds | Gauge Force: | 30 gmf | gmf means gram-force

Three samples were supplied for analysis. These consisted of three polymer resins dissolved in an 80:20 alcohol/water mixture. In each case, the polymer concentration was held constant at 1.75% (active). the samples supplies are listed below.
1.75% amphomer solution (neutralized to 90%)
1.75% PVPNA 735 solution
1.75% POLYQUAT 37

In each experiment, 300 mL of material was applied to the plates. Six experiments were performed per sample.

Initially tack testing produces relatively low forces, as the instrument measures the surface forces of the liquid between the two plates As the solution begins to dry, the polymer can become tacky and more force is required to pull the plates apart. eventually, as the resin dries out, the tackiness decreases and the force needed to pull the plates apart also drops.

Results for the three polymer solutions mentioned above are as follows:

| method 95.0 percent Tukey HSD method polyquat-37 | | |
|---|---|---|
| treatment | count | mean |
| polyquat-37 | 6 | 115.667 |
| PVP/NA | 6 | 471.667 |
| amphomer | 6 | 795.333 |

The above test results are statistically significant at the 95% confidence level and show that polyquat-37 was significantly less tacky than the other two polymers. Specifically, the results clearly show that the highest forces to pull the plates apart result from the amphomer solution. It is concluded that the amphomer solution produces the most tackiness during drying. The PVA/VA (which means poly vinylpyrrolidone/vinyl acetate) gave rise to forces which were approximately half those seen with amphomer. Finally, the polyquat 37 sample shows extremely low forces indicating a virtual lack of any tack.

The following hair tress test was run to determine tackiness of compositions of the invention.
1.) Hair tresses were shampooed with SUAVE CLARIFYING SHAMPOO and rinsed.
2.) Step 1 was repeated.
3.) One gram of composition to be tested was applied to each tress on wet stage and evaluated for tackiness by a panel of five trained judges on a scale of 1 to 10.
In the table below the scale for tackiness was as follows:
LOW tack to HIGH tack
Scale 1 to 10.
In the table below the control was a commercially available leave-on spray-on gel from LAMAUR.

| CONTROL SPRAY GEL | 7, 6.5, 10, 5, 5 | TOTAL = 33.5 |
|---|---|---|
| A | 5, 5, 6, 5, 3 | TOTAL = 24 |
| B | 4, 5, 3.5, 5, 4 | TOTAL = 21.5 |
| C | 5, 7, 6, 5, 3 | TOTAL = 26 |
| D | 6, 4, 5, 4, 5 | TOTAL = 24 |
| E | 8, 9, 6, 8, 7.5 | TOTAL = 38.5 |
| F | 9, 6, 7, 5, 4 | TOTAL = 31 |

From the above data we can conclude that the above compositions containing polyquat 37 at levels 4.0% and below are lower in tack than the control spray gel which contains a commercially used resin. At 5% the tack is higher than the control but could be lowered through the use of auxiliary detackifyers as illustrated in formula F.

Compositions of the invention come in the form of a cream, mousse, gel, a spray-on leave-on product, and a spray-on spritz.

The invention is also related to a method for dressing or styling the hair which comprises placing a small amount of the composition of the invention in the hands, and applying to the hair.

All of the materials which are used in the preparation of the compositions of the invention are either known or can be prepared by known methods. Many of the starting materials used in preparing the compositions of the invention are commercially available.

What is claimed is:

1. An aqueous hair dressing or hair styling composition which comprises about 5.0% polyquaternium 37, propylene glycol dicaprylate dicaprate, and PPG-1 trideceth 6; about 2.5% isopropyl palmitate and about 1.5% isopropyl myristate.

2. A method for dressing or styling hair which comprises placing a small amount of the composition of claim 1, in the hands and applying it to the hair.

* * * * *